United States Patent
Perrin et al.

(10) Patent No.: US 12,422,570 B2
(45) Date of Patent: Sep. 23, 2025

(54) SYSTEM AND METHODS FOR MEASURING PATIENT-SPECIFIC EXTRAVASATION DOSIMETRY

(71) Applicant: Lucerno Dynamics, LLC, Cary, NC (US)

(72) Inventors: Steven Perrin, Durham, NC (US); Joshua G. Knowland, Cary, NC (US); William Gorge, Carmel, IN (US)

(73) Assignee: Lucerno Dynamics, LLC, Cary, NC (US)

( * ) Notice: Subject to any disclaimer, the term of this patent is extended or adjusted under 35 U.S.C. 154(b) by 337 days.

(21) Appl. No.: 18/096,213

(22) Filed: Jan. 12, 2023

(65) Prior Publication Data

US 2023/0243983 A1    Aug. 3, 2023

Related U.S. Application Data

(60) Provisional application No. 63/298,810, filed on Jan. 12, 2022.

(51) Int. Cl.
*A61N 5/10* (2006.01)
*G01T 1/02* (2006.01)
*G01T 1/161* (2006.01)

(52) U.S. Cl.
CPC ............ *G01T 1/026* (2013.01); *A61N 5/1071* (2013.01); *G01T 1/161* (2013.01)

(58) Field of Classification Search
CPC ................ A61N 5/1071; A61N 5/1048; A61N 2005/1074; G01T 1/03; G01T 1/023; G01T 1/026; G01T 1/1606
See application file for complete search history.

(56) References Cited

U.S. PATENT DOCUMENTS

| | | | |
|---|---|---|---|
| 9,002,438 B2 | 4/2015 | Knowland et al. | |
| 9,939,533 B2 | 4/2018 | Knowland et al. | |
| 10,852,446 B2 | 12/2020 | Knowland et al. | |
| 2016/0016008 A1* | 1/2016 | Kelly | A61N 5/103 600/1 |
| 2021/0015434 A1 | 1/2021 | Perrin et al. | |

* cited by examiner

*Primary Examiner* — Don K Wong
(74) *Attorney, Agent, or Firm* — Williams Mullen; Andrew R. Shores

(57) ABSTRACT

A system and method for determining accumulated radiation dose is presented. In some embodiments, the system and method include use of one or more RADFETs to measure and accumulated radiation dose over a desired period of time from an area of interest in a patient. In some embodiments, the one or more RADFETs may be arranged on a test strip, and electrical circuitry provided to selectively couple certain terminals of the RADFETS together to facilitate improved measurement of accumulated dose. A reader may also be utilized wherein the reader may receive a test strip, decouple the electrical connections between select terminals, inject a current into the RADFET and/or measure a voltage from the RADFET corresponding to an accumulated radiation dose.

7 Claims, 8 Drawing Sheets

SYSTEM AND METHODS FOR MEASURING PATIENT-SPECIFIC EXTRAVASATION DOSIMETRY

PRIORITY

This application claims priority to U.S. Provisional Patent Application No. 63/298,810, filed Jan. 12, 2022, the entirety of which is incorporated herein by reference.

FIELD OF THE INVENTION

The present invention relates to systems, devices, and methods of measuring and quantifying extravasation dosimetry in a patient. More particularly, the present disclosure teaches novel systems, devices and methods of determining and/or quantifying dosimetry, namely radiation dose to a patient stemming from, for example, an extravasation during administration of a radiopharmaceutical injection. As will be demonstrated, radiopharmaceutical injection monitoring systems may be utilized to not only for identification and characterization of extravasations, but also dosimetry to determine, among other things, extravasation severity and whether the patient may need to be treated for adverse tissue reactions, among other resulting ailments.

BACKGROUND

Numerous medical diagnostics and therapies today involve the introduction of radiopharmaceuticals into the body, whether it be to enhance nuclear imaging techniques, treat tumors, or other purposes. Oncologists, for example, may be interested in knowing if a prescribed cancer therapy is having an intended effect, in order to improve outcomes, minimize side effects, and avoid unnecessary expenses. Cytotoxic treatments, for example, kill tumor cells. Cytostatic treatments, for example, inhibit cell growth leaving tumors the same size, but preventing the spread of the disease. As another example, immunotherapy treatments use the body's immune system to attack the cancer and initially result in an inflammatory response in the tumor area before there is evidence that the body is effectively attacking the tumor. Historically, measuring the size of the tumor has been a primary way for oncologists to assess treatment effectiveness; however, we now understand that the physical size of the tumor is often not the best or earliest indicator of the therapy effectiveness. For example, with cytotoxic treatment the tumor size reduction only occurs after cancer cells die and the body's natural processes eliminate dead cells; this process can often take weeks. With cytostatic treatment, cancer cells stop growing leaving the clinician unsure of the state of the underlying cancer. With immunotherapy, the body's inflammatory response often masks the tumor from proper evaluation. These are just some of the many challenges facing clinicians today.

The tools presently available to oncologists and researchers to assess tumor response to treatments are not ideal. Palpating the tumor is easy and inexpensive, but it is limited to tumors close to the surface, relies on a physician's memory and notes, and primarily measures physical size. The lack of reproducibility of this palpating process, coupled with historical reasons, contributed to the initial acceptance of significant changes in tumor size as an indicator of therapy assessment. Wolfgang A. Weber, et al., "Use of PET for Monitoring Cancer Therapy and for Predicting Outcome," 46 J. Nucl. Med. (No. 6) 983-995 (June 2005). Structural imaging tools (CT, MRI, x-ray) provide more precise measurements for tumors both close to the surface and in deep tissue, but again primarily measure size, which is not an ideal indicator. Molecular imaging (single-photon emission computerized tomography (SPECT) or PET/CT scan, for example) may measure the emissions from injected radio-labeled tracers captured by live cancer cells and is routinely used for pre-therapy staging of cancer. Visually identifying metastatic disease is the primary means of staging cancer; however, semi-quantitative measurements, for example the Standardized Uptake Value (SUV), may also be used to stage cancer and other conditions. For example, semi-quantitative measurements may be used to help determine whether lung nodules are malignant, or brain function is deteriorating. In general, semi-quantitative measurements may include a ratio of the amount of radio-labeled tracer in an area of interest (e.g., a tumor) compared to the level in a reference area, for example the rest of the body. For example, while molecular imaging is one primary tool for the pre-therapy need to stage a patient's cancer, it is also rapidly becoming the most advanced tool for oncologists and researchers to assess tumor response, since molecular imaging can capture the metabolic or proliferative condition of the cancer and/or the size of the tumor. Using measurements taken from the staging metabolic imaging scans and then comparing these values to a follow-up imaging scan is currently one of the best available indicators for therapy effectiveness. Other imaging techniques are available as well and are known in the art.

Despite the increasing trend to use comparative molecular imaging scans in assessing response in more and more conditions as clinical evidence continues to grow, there are still limitations with this assessment tool. For example, molecular imaging scans are expensive, and their use is often challenged based on cost. Additionally, there are several issues with semi-quantitative measurements such as SUV. According to Dr. Dominique Delbeke: "[t]he reproducibility of SUV measurements depends on the reproducibility of clinical protocols, for example, dose infiltration, time of imaging after 18F-FDG administration, type of reconstruction algorithms, type of attenuation maps, size of the region of interest, changes in uptake by organs other than the tumor, and methods of analysis (e.g., maximum and mean)." Dominique Delbeke, et al., "Procedure Guideline for Tumor Imaging with 18F-FDG PET/CT 1.0," 47 J. Nucl. Med. (No. 5) 885-895 (May 2006). +

Infiltrated injection (extravasation) of radio-labeled tracer is an exemplary complication that often goes unnoticed by clinicians. Medhat Osman, "FDG Dose Extravasations in PET/CT: Frequency and Impact on SUV Measurements," Frontiers in Oncology (Vol. 1:41) 1 (2011). An infiltration is a common problem that can occur when the radio-labeled tracer infuses the tissue near the venipuncture site and can result from the tip of the catheter slipping out of the vein or passing through the vein. Additionally, the blood vessel wall can allow part of the tracer to infuse the surrounding tissue. By some estimates, extravasations occur with alarming frequency as high as ~10%. As a result, the radio-labeled dose being delivered is inaccurate and thus so are the SUV calculations, which can severely impact patient treatment and research conclusions. These infiltrations may in fact contribute to the wide variability in researchers' efforts to characterize SUV thresholds for clinical decision making. In one study, it was determined that the "thresholds for metabolic response in the multicenter multiobserver non-QA settings were −34% and 52% and in the range of −26% to 39% with centralized QA". Linda M. Velasquez, et al., "Repeatability of 18F-FDG PET in a Multicenter Phase I Study of Patients with Advanced Gastrointestinal Malignancies," 50 J. Nucl. Med. (No. 10) 1646-1654 (October 2009). In local practices and even in practices and research centers employing Quality Assurance checks, these issues with SUV calculations have left oncologists and researchers needing to see significant changes in SUV values to be somewhat assured they are making sound treatment decisions or reaching proper research conclusions.

Equally concerning, however, is the potentially significant radiation dose to underlying tissue and skin that can unknowingly result from the extravasations. These effects have only been minimally studied, but are known to cause both short-term and long-term damage, including damage that is initially difficult to detect, diagnose, and treat. To be sure, undetected extravasations often lead to radiation exposure that exceeds established safety thresholds.

In light of the problems associated with current measurement and prediction systems, methods and systems for identifying improperly administered radio-labeled tracer injections (infiltrations or extravasation), which negatively impact tissue uptake and SUV results, and easier, less costly, and more efficient systems and methods for measuring and predicting the status and/or changes in such biological processes have also been developed. For example, methods and systems for detection of radioactive materials in the body over a desired period of time are disclosed in, for example, U.S. application Ser. No. 15/885,112 filed Jan. 31, 2018, now U.S. Pat. No. 10,852,446, which is a divisional of U.S. application Ser. No. 14/678,550 filed on Apr. 3, 2015, now U.S. Pat. No. 9,939,533, which is a continuation-in-part of U.S. application Ser. No. 13/840,925 filed on Mar. 15, 2013, now U.S. Pat. No. 9,002,438, which claims the benefit of priority to U.S. Provisional Application No. 61/653,014, filed on May 30, 2012. Each of these disclosures are incorporated fully herein by reference.

Certain aspects of the systems and methods disclosed in the references identified above relate to, among other things, the detection and quantification of infiltrations during injections of radio-labeled radiotracers (i.e., non-bolus injections). In nuclear medicine procedures, radiopharmaceuticals are typically injected intravenously. For many of these procedures, the injection should be administered as a bolus that results in complete and prompt systemic distribution of the radiopharmaceutical. An extravasation, or infiltration, occurs when an injected substance leaks into surrounding tissue instead of remaining within the vasculature as intended. Extravasations can be caused by improper placement of the intravenous access (IV), erosion or degradation of the vessel wall, and/or failure of vessel integrity. When any radiopharmaceutical is extravasated, some of the activity remains at the injection site instead of circulating throughout the patient's body. Extravasations reduce the net available activity for uptake and alter the uptake kinetics for subsequent imaging. Extravasations may also undesirably expose tissue surrounding the extravasation to unacceptable doses of radiation.

It may therefore be advantageous to utilize, in some embodiments of the present disclosure, methods and systems for estimating the initial magnitude of an infiltrated injection, and to measure the rate of clearance of some or all of the infiltrated portion to the bloodstream, etc., over a critical time period. Some such systems and methods are disclosed, for example, in U.S. Patent Pub. No. 2021/0015434 titled System and method of using temporal measurements of localized radiation to estimate the magnitude, location, and volume of radioactive material in the body, and the related disclosures discussed and incorporated therein, each and every one of which are incorporated herein by reference. Using such tools, it may be possible to quantify a clearance rate to better quantify, for example, radiation dose to certain affected tissue. Of course, clearance rate is only one of the factors relevant to the dosimetry calculations desired and discussed herein. Others include infiltrated tissue volume, and radioactivity distribution, retention, and absorption.

Existing dosimetry techniques may not be suitable for extravasations because they do not accurately account for changes in extravasated activity or volume over time. As explained in some exemplary embodiments herein, scintillation detectors that record time-activity curves (TACs) of the activity near the injection site may be a practical way to gather this information. For example, the rate of biological clearance of the extravasate may be determined with TAC data. Using this rate, along with the total extravasated activity that may be determined using, for example, nuclear imaging or direct measurement of the magnitude, location, and/or volume of the infiltration at a given point in time, initial extravasation activity may be estimated by extrapolating back to the time of injection.

One aspect of the methods and systems described is to have an understanding of the magnitude/amplitude, location, and/or volume of, for example, an infiltrated portion of a radio-tracer injection as a function of time. Presently, such information may be determined by using, for example, nuclear medicine imaging techniques (e.g., PET scan). However, there are many circumstances where it may be advantageous to determine this information without relying on the nuclear medicine image or scanner itself. For example, the radioactive source of interest may be outside the imaging device's field of view, or may not be able to be determined until after the radioactive source has dissipated or moved, etc. It may also be advantageous to determine this information without relying on an expensive nuclear imaging system (e.g., PET scan, etc.). For example, such systems, devices and methods discussed herein may be used to quantify and otherwise understand the uptake of radioactive material in a tumor over time, precise organ dosimetry of radiopharmaceuticals, uptake of radiopharmaceuticals in other areas of interest in the body (e.g., brain (basil ganglia), other organs, other tissues, etc.), and other circumstances. Further, existing nuclear imaging techniques may not be capable of detecting certain types of radiation used in certain radiotherapies, such as for example alpha and/or beta particles, which may be of particular interest given the relatively significant damage such particles can impart on living cells.

It is therefore an additional object of the present disclosure to provide a method and system of measuring or estimating the amplitude, location, and/or volume of a radioactive source in the body—both as initially detected and how such characteristics may change over time—without relying on a nuclear medicine imaging device like a PET scanner and the like. Instead of using the nuclear medicine imaging device (e.g., SPECT or PET scanner) itself to make the necessary measurements, one or more sensors may be used to measure, for example, radiation activity over a period of time. For example, sensors such as those taught in U.S. Pat. Nos. 9,002,438 and 9,939,533 may be used, though other sensors for measuring radiation activity may also be utilized. Then, utilizing systems and methods of the present disclosure, information obtained by the sensor (s) may then be used to measure, determine and/or estimate the amplitude of a radioactive source in the body over a period of time of interest, in addition to the location and/or volume of a radioactive source, and may also characterize the rate of change of such characteristics over the relevant period of time. Such information may also be used to estimate a dose of radiation to surrounding tissue and/or skin. While radiation dose to the skin may be measured using techniques disclosed here, the present disclosure advantageously also enables measurement of radiation dose to volumes of tissue within the body (i.e., not just skin exposure, but also exposure to tissue below the skin and otherwise inside the body, etc.).

SUMMARY

In some embodiments, an exemplary method of determining patient-specific extravasation dosimetry is presented which may include the steps of determining a count-rate curve over a time-period of interest using one or more radiation probes positioned proximate a region of interest, determining a calibration factor for converting the count-rate curve to an absolute activity curve, wherein the calibration factor is determined by dividing the count rate at an imaging time by total activity from the region of interest (such as for example, as measured by an imaging device), determining an absorbed energy fraction based on tissue characteristics and the size and location of the region of interest, and determining absorbed dose to infiltrated tissue by summing total energy emitted in region of interest based on the count rate curve and calibration factor and absorbed energy fraction.

In some embodiments, a method of determining patient-specific extravasation dosimetry is presented that may include determining an accumulated dose curve over a time-period of interest using one or more radiation test strips positioned proximate a region of interest, determining a calibration factor for converting the accumulated dose curve to an absolute dose curve, wherein the calibration factor is determined by dividing the instantaneous dose at an imaging time by total activity from the region of interest, determining an absorbed energy fraction based on tissue characteristics and the size and location of the region of interest, and determining absorbed dose to infiltrated tissue by summing total energy emitted in region of interest based on the accumulated dose curve and calibration factor and absorbed energy fraction.

Such methods may also include a plurality of RADFETs on the test strips. The RADFETs may be electrically coupled together, and in some embodiments selectively electrically coupled together, if desired.

In some embodiments, such methods may include the step of removing the one or more test strips from the patient after the time-period of interest and inserting the test strips into a reader, wherein the reader may be configured to sever the electrical connection between the terminals of the plurality of RADFETs, inject a current into each of the plurality of RADFETs, and measure a voltage at each of the plurality of RADFETs. In some embodiments, a reader may be used to read the dose, and also facilitate the severing of the electrical connections. In some embodiments, the electrical connections may be reconnected after being severed to facilitate continued measurement of accumulated dose or other desired measurement. Such methods may also utilize a display or other device to display or otherwise record, present, or communicate information about the measured dose, etc.

In certain other embodiments, a system for measuring accumulated radiation dose is presented. The system may include, among other things, one or more RADFETs configured to measure an accumulated radiation dose over a measurement period, circuitry for electrically coupling select terminals of the one or more RADFETs together during the measurement period, and/or a reader for reading the accumulated radiation dose after the measurement period. In some embodiments, the reader may include an electrical decoupling mechanism for disconnecting the electrical coupling of the select terminals, and a voltage sensor for measuring a voltage corresponding to the accumulated radiation dose. The system may also include a current source for injecting current into each of the one or more RADFETs to facilitate measurement of the accumulated radiation dose.

The electrical decoupling mechanism may include a mechanical mechanism for physically severing the electrical connections, a solvent for physically severing the electrical connections, or an electrical mechanism for electrically severing the electrical connections, including for example electrical switches, transistors, diodes, or the like.

In some embodiments, the one or more RADFETs may be arranged on a test strip, and the test strip may optionally be positioned near an area of interest, including for example on a patient. The test strip may be measured in place, or may be configured to be removed from the area proximate the area of interest and inserted into a reader for reading the accumulated radiation dose. The RADFETs and/or test strips may be arranged in any desired geometry, including in a cuff sized to fit a patient's arm, a belt to wrap about a patient's torso or abdomen, or a helmet to fit proximate a patient's head.

The system may also include an output for communicating information, including accumulated does, temperature compensation information, test strip information, or other useful information. The system may also be configured to re-couple the severed electrical connections following a determination of accumulated dose. The system may also include a processor and memory, or computer or other similar device for recording and storage information from the system, and calculating dose curves and the like as discussed herein.

DETAILED DESCRIPTION

Figure 1:
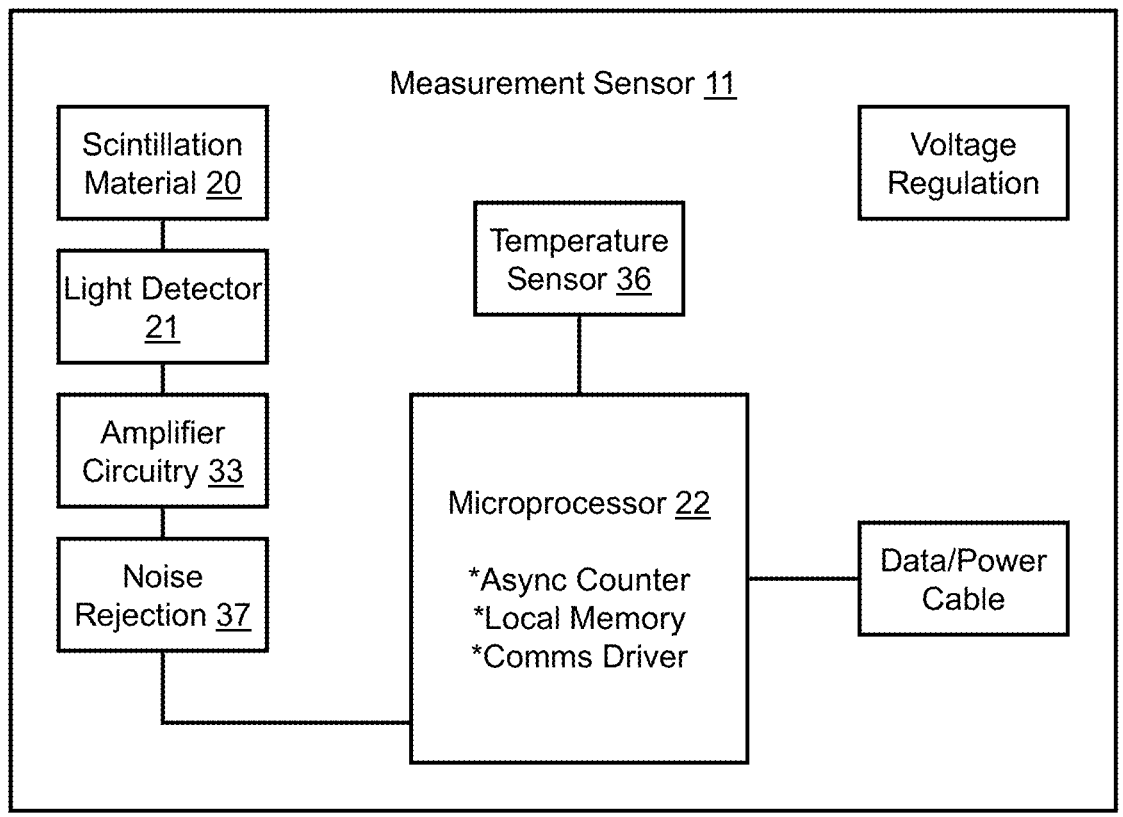
FIG. 1 is an exemplary schematic of a measurement sensor according to some embodiments of the present disclosure.
Figure 2:
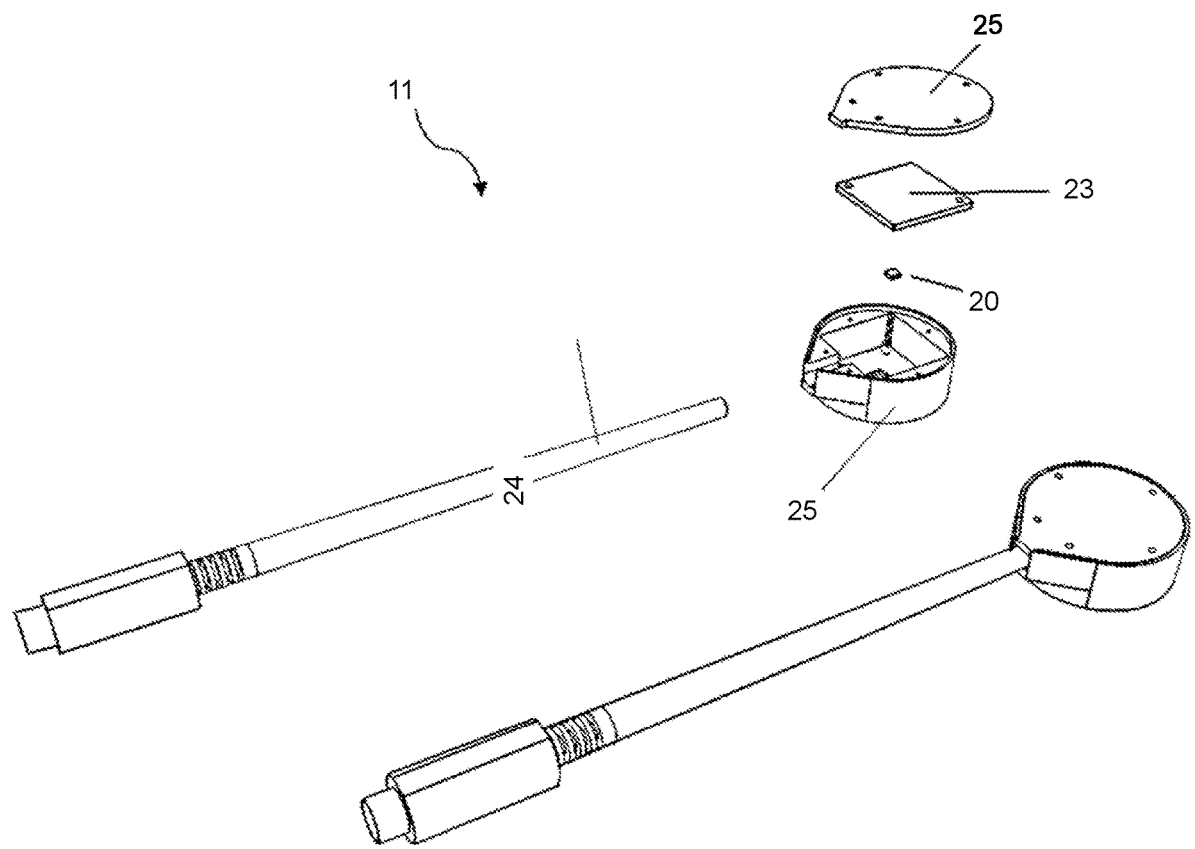
FIG. 2 is an exemplary illustration of a measurement sensor according to some embodiments of the present disclosure.
Figure 3:
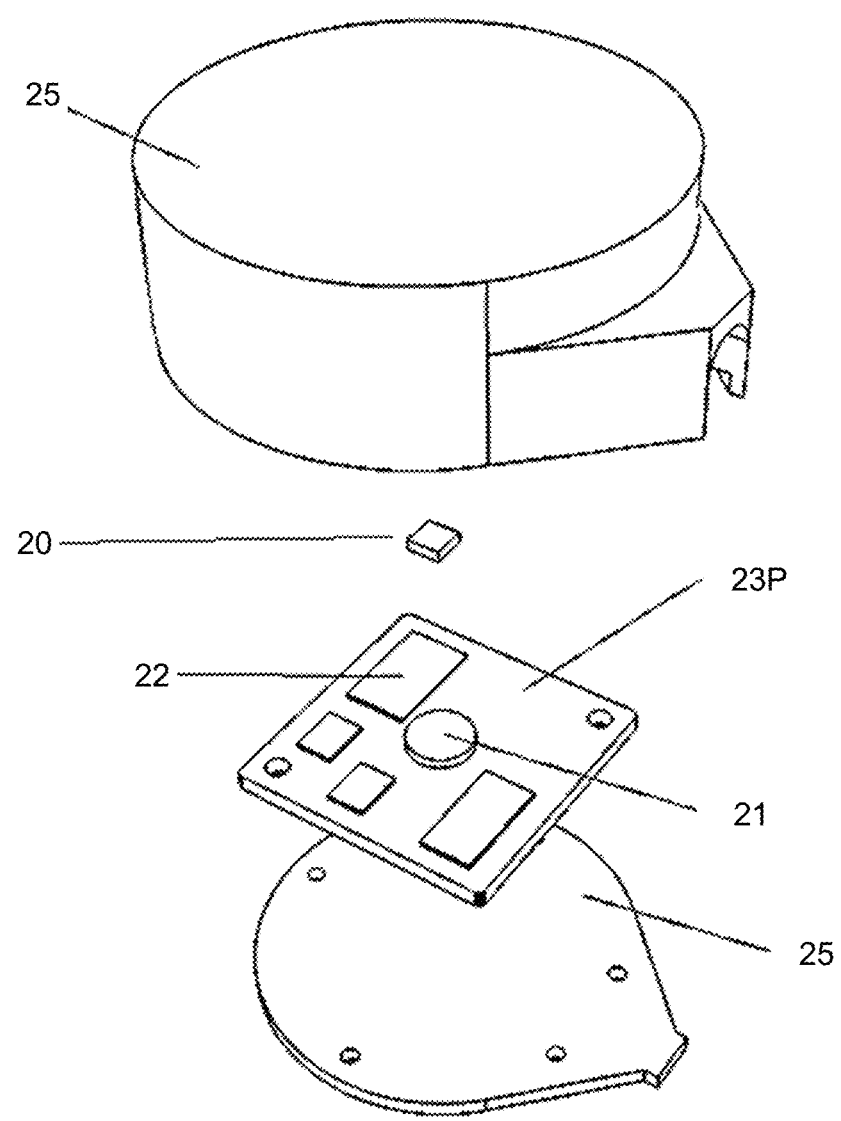
FIG. 3 is an exemplary illustration of a measurement sensor according to some embodiments of the present disclosure.

The present disclosure teaches, among other things, systems and methods for determining patient-specific extravasation dosimetry. In some embodiments, dosimetry may be determined, at least in part, using uptake probe measurements. This technique may include, for example, using one or more of a variety of radiation probes to measure radiation activity as a function of time (i.e., a time-activity curve or TAC), and use sequential images or other techniques to determine volume of the radioactive source over time, or other radiation source volume estimation techniques. Such techniques may also utilize methods and other mechanisms to account for other aspects of the anatomy being measured, and the different characteristics thereof (bone, skin, etc.).

In other embodiments, imaging alone may be employed (e.g. PET or SPECT scans), where the known half-life of the radiopharmaceutical is used to estimate dosimetry, but without having the benefit of knowing the clearance/reabsorption characteristics.

In other embodiments, less robust but nevertheless sufficient methods of determining radiation activity over time may be utilized, including for example, calibrated, radiation-sensitive semiconductors such as, for example, RADFETs. Such alternative probes may be utilized to determine accumulated radiation over a period of time which may also be used to determine dosimetry of a patient. Additionally, using certain novel techniques disclosed herein, traditional RADFETs, for example, may be modified to enable the accumulated dose readings to be iteratively sampled to provide, an understanding of dynamic accumulation of dose over time, which may also be advantageous in determining patient dosimetry.

Radiation Probes

According to some exemplary embodiments, one or more radiation detectors may be utilized to quantify detectable radiation as a function of time. By way of one example, the detector may include a scintillation detector that may include, for example, a scintillation crystal (for example, bismuth germanate or comparable) that produces light in response to radiation emitted from the body in the presence of radioactive material (through positron annihilation, beta decay, or electron capture, for example, among others).

For example, localized radiation detectors such as those disclosed U.S. Pat. Nos. 9,939,533 and 9,002,438 may be used to measure activity at the injection site as a function of time (i.e. time-activity curve or TAC). Referring now to FIGS. 1-4, a measurement sensor 11 may be utilized that may include, for example, a scintillation material 20; a light detector 21; and a sensor processor 22 with associated non-transient sensor memory 30, logic or sensor software, and other circuitry supporting these components in operable communication, optionally with a printed circuit board. Such sensors may also include amplifier circuitry 33 and/or a temperature sensor 36. Measurement sensor 11 may utilize a scintillation material 20 to receive radiation and convert the radiation into other forms of energy, such as pulses of light, which may then be detected, for example by the light detector 21. The sensor processor 22 may enable measurement and collection of the photons, such as the number of light pulses detected over a given amount of time. Optionally, noise rejection 37 may be included that may provide a filter for filtering amplified signal data based on the height or amplitude of such pulses. For example, noise rejection 37 may include a voltage comparator or an analog to digital converter with computer program code to compare the digital output to a reference level.

Possible scintillation materials 20 include, but are not limited to: Bismuth Germanate (BOO); Gadolinium Oxyorthosilicate (GSO); Cerium-doped Lutetium Oxyorthosilicate (LSO); Cerium-doped Lutetium Yttrium Orthosilicate (LYSO); Thallium-doped Sodium Iodide (NaI(T1)); Plastic Scintillator (Polyvinyltoluene); or Cadmium Zinc Telluride (CZT). In an exemplary embodiment of a measurement sensor 11, multiple scintillation materials 20 adapted to measure different radiation energies may be used. In another embodiment of a measurement sensor 11, scintillation materials 20 that do not require the use of a light detector 21 may be used. In another embodiment of a measurement sensor, multiple scintillation materials 20, each with their own detection circuitry, may be included to enable a two- or three-dimensional array of measurements.

Of course, other radiation sensors known in the art may be utilized as desired. For example, radiation sensors capable of detecting alpha particles, beta particles, x-rays, gamma rays or any other kind of radioactive decay particle/energy may be utilized depending on the desired application. Measurement of beta particles, for example, may be advantageous when assessing delivery of a radio-therapeutic to an area of the body as such drugs sometimes release beta particles. It may similarly be advantageous to ensure that certain beta particle (or other particle) emitting drugs or other substances not reach a certain part of the body. Thus, sensors could be used to confirm the absence of such substances. All that is typically necessary for the sensors, in some embodiments, is that the sensor be capable of detecting emissions from radioactive material, and further capable of transmitting or otherwise sharing information about those emissions to the system for processing. It may also be desirable, in some embodiments, that the sensors and/or system generally be able to measure an energy level associated with the detected emissions, or filter received energy above or below a certain threshold, and/or between two or more thresholds, etc.

Utilizing measured data, the rate of reabsorption into the bloodstream may be calculated by observing the activity at the detector as a function of time (i.e. the rate at which radioactive activity leaves the infiltration site). Knowing from the TAC the amount of radioactive material at a time t, and the rate at which it left the infiltration site, an estimate of the clearance rate may be determined. Knowing the clearance rate, as discussed in greater detail below, can help better estimate the dosimetry to the patient from the extravasation.

In some embodiments, the radiation detector may record particle counts per second (cps) and generate a plot of counts vs. time. Additionally, in some embodiments, one or more of the probes may be positioned at or near the radiopharmaceutical injection site, and one or more additional detectors may be positioned away from the injection site (e.g., on the opposite arm, etc.) to provide a reference measurement. This reference measurement may be subtracted from the one or more detectors at or near the injection site to account for counts generated, for example, in areas outside the region of interest (for example, originating in the patient's torso or other areas of the body).

Modified RADFETs

According to certain embodiments of the present disclosure, the radiation probes used may be less complex than those discussed above and still yield the information for determining dosimetry and, in certain preferred embodiments, whether an extravasated patient is at risk. In one exemplary embodiment, one or more Radiation sensitive Field Effect Transistors (RADFETs) may be utilized. In general, RADFETs include physical properties that may be physically altered in response to radiation exposure. The magnitude of the exposure may then be measured or otherwise determined, yielding information about the magnitude, etc., of the radiation desired to be measured (e.g., radiation emitted from an extravasation). For example, in some embodiments, electrical properties of the RADFETs may be utilized to determine properties of the radiation to which the RADFET was exposed. In some instances, RADFETs may be able to utilize electrical properties to measure radiation exposure on the order of 0.003 Gy. Of course, development in this area continues to improve and even more sensitive RADFETs may be developed, which are contemplated in this disclosure.

Unlike the radiation probes discussed generally above, embodiments of the RADFETs contemplated herein generally yield information regarding an accumulated dose of radiation rather than counts per unit time like certain of the exemplary probes discussed herein. Thus, for example, a RADFET positioned proximate a patient during an extravasation event may ultimately yield information regarding total radiation dose at the location of the RADFET over the time period it was exposed, but not for example how the rate of exposure fluctuated over the exposed time period. Thus, without modification or use of techniques not currently employed in the art, typical RADFETs may not provide insight into, for example, the clearance rate or other such information.

Figure 4:
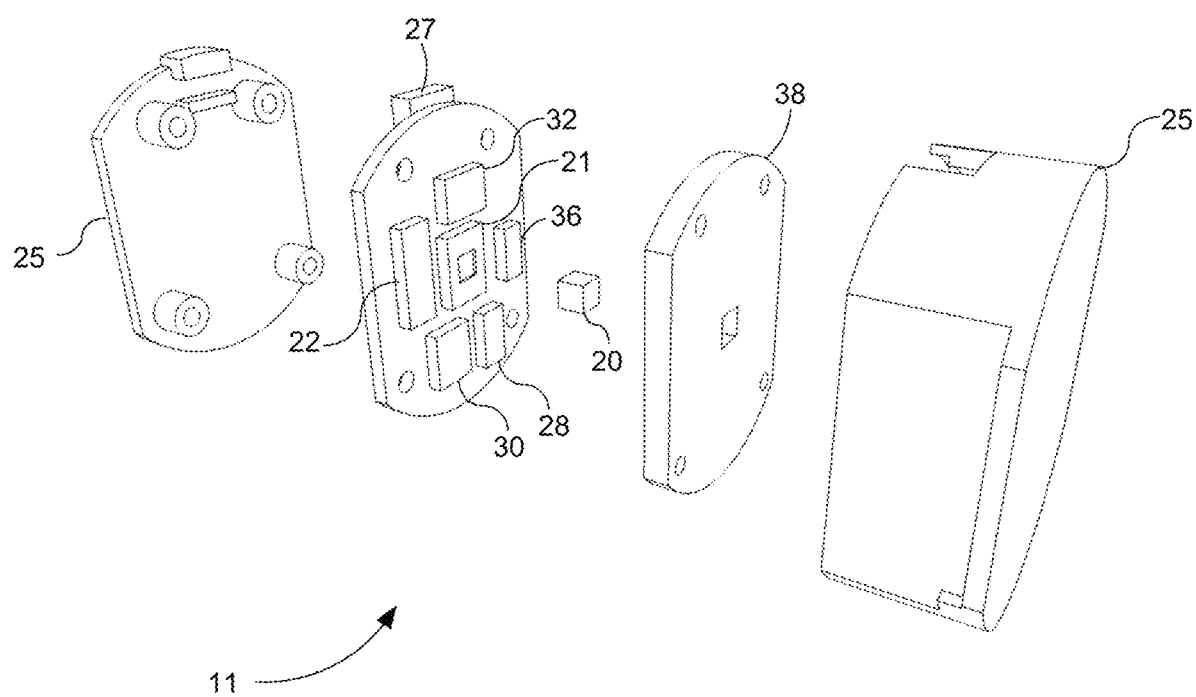
FIG. 4 is an exemplary illustration of a measurement sensor according to some embodiments of the present disclosure.
Figure 5:
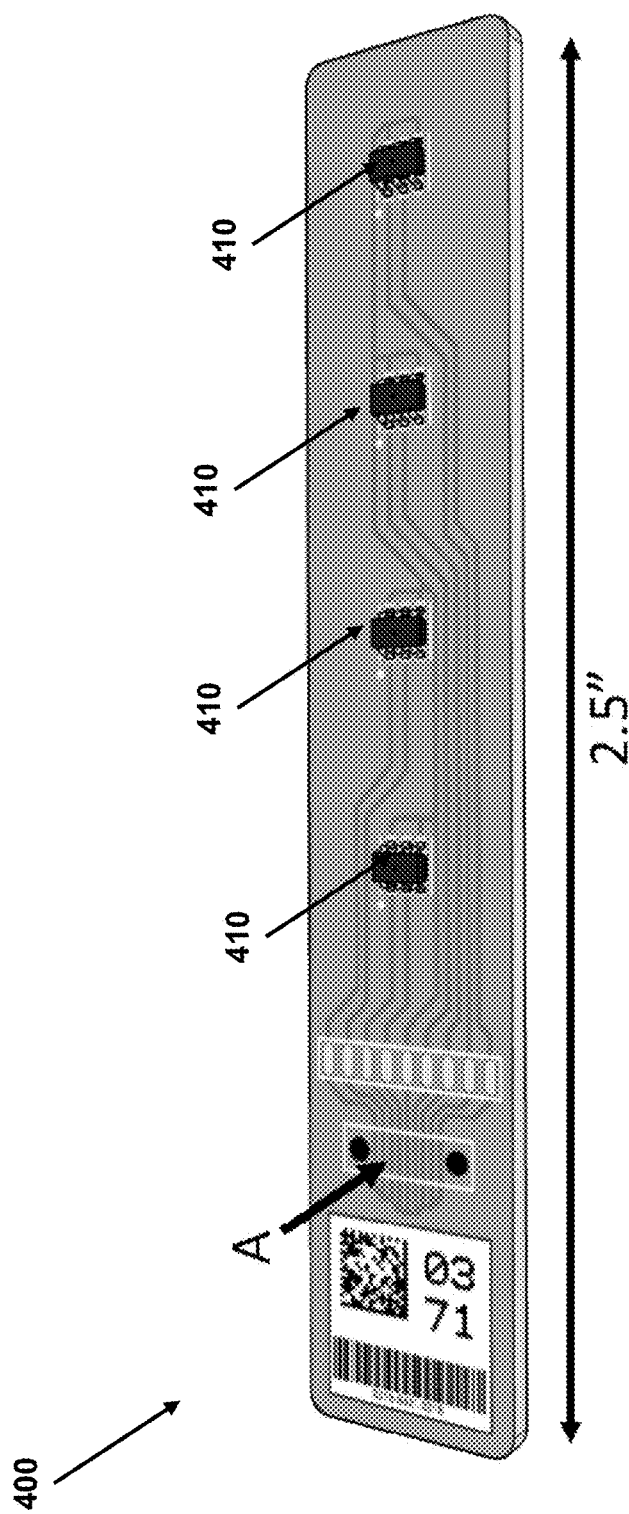
FIG. 5 is an exemplary illustration of a test strip according to some embodiments of the present disclosure.

In some embodiments, it may be advantageous to utilize a plurality of RADFETs for, among other reasons, redundancy and measurements at different locations relative to the patient and/or extravasation site. Referring now to FIG. 4, an exemplary test strip 400 is presented having a plurality of RADFETs 410. The RADFETs 410 may be distributed on the test strip 400 in any arrangement desired, including various geometries and/or at known distances relative to one another and/or an injection site or other patient specific marker. The exemplary embodiment in FIG. 4 illustrates four RADFETs 410, but those skilled in the art will appreciate that any number of RADFETs, including substantially more or as few as one, may be utilized. In some embodiments, the test strip 400 may have a general overall length on the order of approximately 2.5 inches as noted in FIG. 4, but test strips of any size, shape, or arrangement are contemplated in this disclosure. For example, the test strip 400 may have a size and shape corresponding substantially to the footprint of a single RADFET 410, or alternatively may correspond to a size of a typical patient arm, head, limb, etc. on which the test strip may be desirably placed. Other sizes and/or arrangements, both larger and smaller, may also be utilized.

Figure 6:
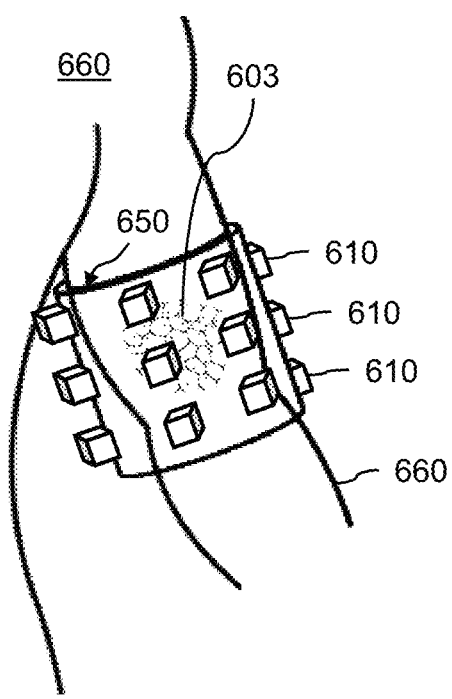
FIG. 6 is an exemplary sensor configuration according to some embodiments of the present disclosure.
Figure 7:
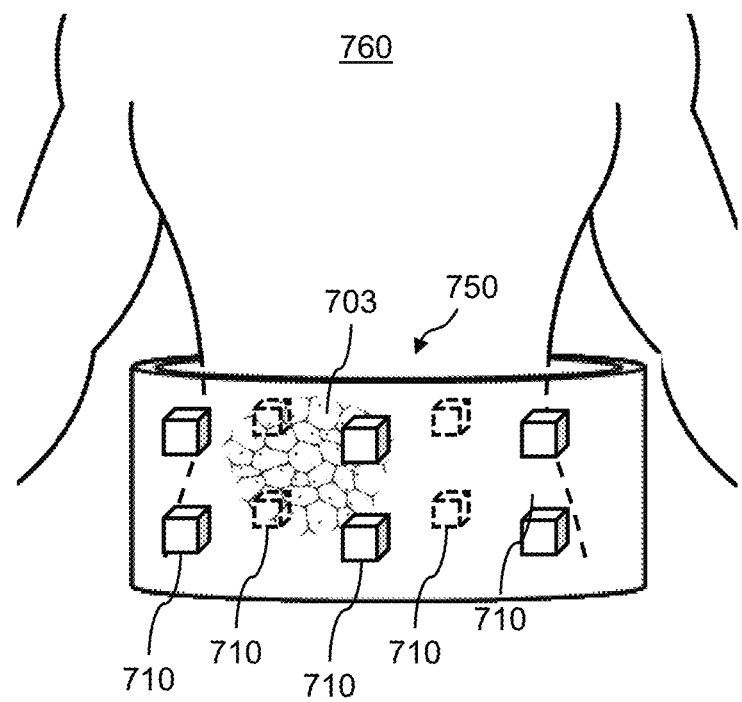
FIG. 7 is an exemplary sensor configuration according to some embodiments of the present disclosure.
Figure 8:
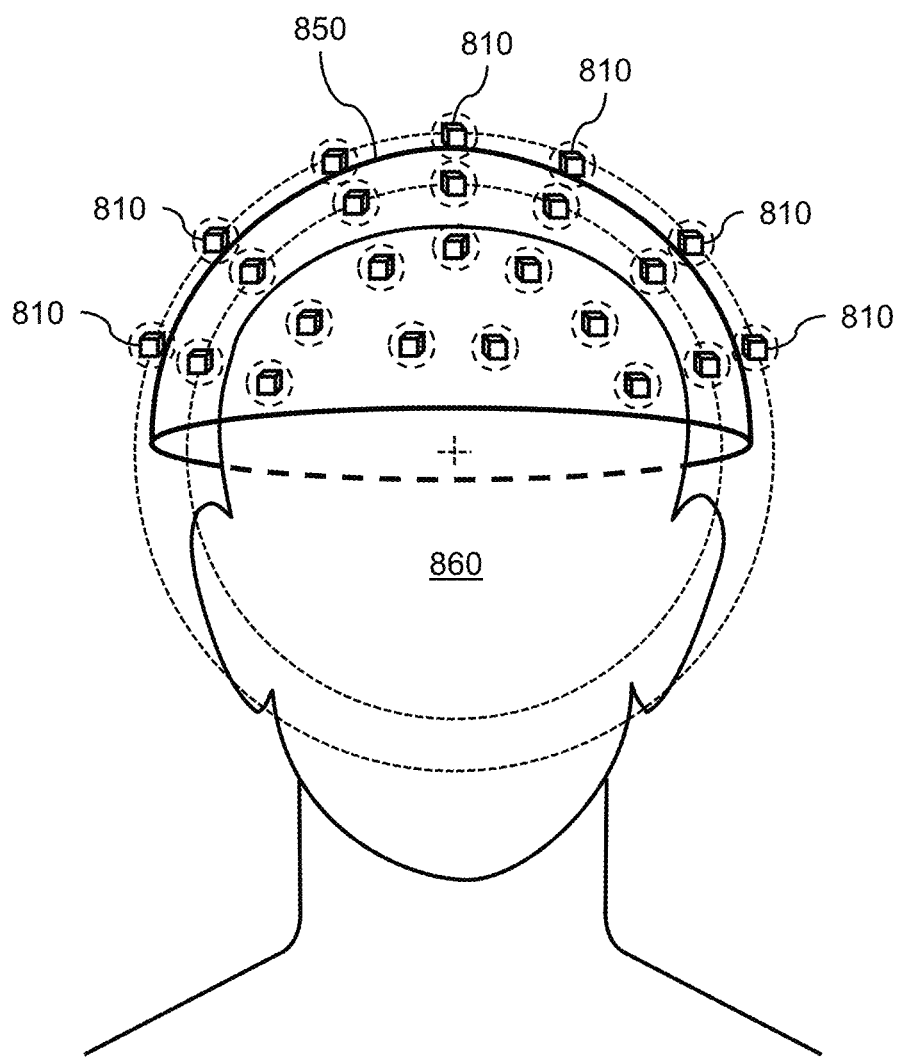
FIG. 8 is an exemplary sensor configuration according to some embodiments of the present disclosure.

Test strip 400 may also include three dimensional geometries, such as for example those discussed in U.S. Patent Publication No. 2021/0015434. For example, FIG. 6 presents an exemplary embodiment 600 of an arrangement of RADFETs 610 on a cuff 650 sized to fit the arm of a patient 660 near an area of interest 603. FIG. 7 shows an alternative arrangement positioned about the abdomen of a patient 760 wherein RADFETs 710 are positioned on a cuff 750 proximate area of interest 703. FIG. 8 presents another exemplary embodiment that may include a similar arrangement for positioning RADFET's 810 on a helmet 850 for positioning about a patient's head 860.

One exemplary embodiment of a test strip 400 may include a flexible circuit board material that may also include an adhesive backing enabling, for example, adhesion of the test strip 400 onto a patient or other desirable surface. As one non-limiting example, in some embodiments, it may be desirable to attach test strip 400 directly onto a patient's skin proximate an injection site or other area of interest.

In embodiments where a plurality of RADFETs are utilized, it may be that the RADFETs each perform better (more sensitive, better accuracy, etc.) when the terminals of each RADFET are electrically coupled together. For example, by coupling the terminals of the RADFETs together, a field across the oxide layer may be more constant, thereby improving RADFET detection accuracy. Functionally this is generally not a problem given that RADFET strips (e.g., test strip 400 or those configurations shown in FIGS. 6-8, for example) like those contemplated herein for use in proximity to a patient's injection site may be configured accordingly. For example, as shown in FIG. 4, test strip 400 may include circuitry, wiring, or other features to electrically couple the terminals of each RADFET 410 in a manner to optimize their measurement characteristics. Similar configurations may be arranged for other geometries like those shown in FIGS. 6-8. In general, any electrically coupling technique may be utilized as desired by the user.

However, to determine the dose to a particular RADFET at any given time for some of the RADFETs contemplated herein (e.g. RADFET 410), an electrical current may need to be injected into one or more terminals of the RADFET 410 and a voltage then measured at one or more terminals, for example. Thus, in some embodiments, it may be necessary or at least desirable to have one or more methods and/or mechanisms for breaking the electrical connection between the terminals of a RADFET 410, and efficiently inject current and/or read a voltage from one or more of the RADFETs 410. In some embodiments, this may be done manually, for example by cutting or otherwise decoupling the terminals, injecting current, and reading a voltage. The user may then utilize the measured voltage to determine the accumulated radiation dose.

To determine accumulated dose more efficiently, however, in some embodiments, test strip 400 may be configured to interact with a "reader" or other device into or onto which test strip 400 may be inserted or placed. The reader or other device may then facilitate one or more of de-coupling the electrical connections between the terminals of one or more RADFETs 410, injecting current into one or more RADFETs 410, and/or reading a voltage of one or more RADFETs 410.

Readers contemplated by this disclosure could take many forms. For example, one such reader may be configured to interact with a test strip that is itself configured to adhere directly to a patient's skin proximate, for example, an injection site (such as for example test strip 400). In some embodiments, after the injection, or at some desirable or pre-determined time thereafter, the test strip (e.g. test strip 400) may be removed from the patient and inserted into or otherwise engaged with the reader.

In this one exemplary embodiment, the reader may include a mechanism for permanently or temporarily severing the electrical connection between the terminals of one or more RADFETs 410 to facilitate reading the dose on each of the RADFETs 410. For example, the reader may include a cutting mechanism or other similar device to physically sever electrical connections as needed. Referring to exemplary test strip 400, the electrical connections may be severed in region A by, for example, stamp-cutting the connections. Of course, any method known in the art for permanently or momentarily interrupting an electrical connection may be utilized, including but not limited to cutting, abrading, tearing, or burning the connections Additionally, electrical connections between terminals may be interrupted by chemical means including, for example, etching, dissolving, or vaporizing. And additionally, electronic methods may be used to interrupt the electrical connections between terminals such as, for example, switching with a relay, transistor, or other switch device or by intentionally overloading a fuse or thermostat to cause an open-circuit condition, among other techniques.

In some embodiments, the reader may also include electrical circuitry or other similar or related components of its own that may facilitate one or more of injecting a current into one or more of the RADFETs 410 on test strip 400, and/or reading a voltage of the RADFETs 410. The reader may also include circuitry, processors, communication ports (wired and/or wireless) and/or other mechanisms to convert a measured voltage, for example, to a dose reading, and/or communicate the dose measured (or other information (voltage, current, coupling status, etc.) to a user or other device, either via a display or other indicator, and/or otherwise output such information. In some embodiments, the reader may include one or more lights, sounds, or other indicators that may be utilized to indicate measured dose at, above, below and/or in between one or more thresholds, for example.

In some circumstances, it may also be useful to include a mechanism or other aspect such that a test strip, once measured or otherwise after its use is completed, may be automatically destroyed or at least rendered incapable of further use. This may ensure, among other things, that test strips intended only for a single use are not inadvertently reused. Among other benefits, such mechanisms could help reduce the risk of inter-patient infection or cross-contamination, and protect measurement accuracy generally. Of course, in some embodiments, re-usable test strips may be utilized. For example, a test strip may be used with a first patient, and measurements taken as taught herein, and then used with a second patient by measuring an initial baseline dose already accumulated by the test strip and calibrating the subsequent measurements accordingly, for example.

In some embodiments, for example, in a manner similar to the severing of the electrical connection between RADFET terminals discussed above, a vital connection on the test strip could be cut, torn, otherwise destroyed, etc. after the reader has successfully measured each RADFET's dose. Alternatively, sufficiently high electrical current or voltage could be injected into each RADFET after measurement to render the RADFET incapable of further use. Other means could be employed as well, such as an indicator to the user or an electrical cut off mechanism, or a component or other feature of the reader and/or software therein that recognizes the test strip and can determine that the strip has already been used, for example.

In certain other embodiments, a modified reader may be employed having features to enable the taking of more robust measurements while still using simplistic technology such as RADFETs, for example. For example, the reader may be configured to, for example, attach onto or near the patient (or other area of interest). Such a reader may be an "active" reader in that it may include a power source (or be configured to be coupled to a power source), and be configured to receive a RADFET patch, including for example a disposable or reusable RADFET patch.

In some embodiments, the modified reader may be configured to switch between multiple modes. For example, a first mode may configure the reader and RADFET patch such that the RADFETs are electrically coupled such that the RADFETs are in the preferred configuration to accumulate dose. The reader may also have a second mode in which the RADFETs may be measured to determine the accumulated dose (e.g., the RADFETs may be electrically decoupled, a current injected, and a voltage measurement taken so as to determine, according to the specification of the RADFET being utilized, how much radiation dose has been accumulated). The sensor may then be configured to switch back to the first mode to enable the RADFETs to continue to accumulate dose.

Any mechanism for switching between the electrically coupled state and the decoupled state wherein current may be injected and a voltage measured to determine dose, may be utilized. Those include mechanical switching methods that sever and reconnect the terminals as needed, or electrical switching methods using electronic switches, relays, etc. A processor or other controller mechanism may be included to drive the switching mechanism.

In such a configuration, the reader device and RADFET patch may enable the generation of a time-dose curve comparable to the count-rate curve discussed above. In a similar manner, then, a clearance rate and other useful information about a potential extravasation may be determined, and more refined estimates of radiation dose to tissue and/or skin may be determined, similar to those discussed hereinabove. Such embodiments are therefore advantageous relative to devices that may provide only single dose measurements received over a fixed period of time. Sequences of measurements, like those contemplated in some embodiments herein, can provide additional data (clearance rate, etc.) enabling determination of radiation dose to a volume of tissue beneath the skin, for example, as disclosed herein.

In some embodiments, the various readers contemplated herein may be compatible with a plurality of various test strips 400, including test strips that may include various different RADFETs with different specifications, for example. To accommodate this variety, the reader may also include one or more mechanisms for determining the type of RADFET test strip 400 being utilized, and/or the specific RADFET(s) included on the test strip 400. The reader may then be further configured to alter its electrical decoupling, injection current, and/or voltage measurement techniques, among other things, according to the test strip configuration being utilized. By way of just one example, the reader may include a bar code scanner, camera, RFID reader, or other mechanism to read a bar code, visual identifier, or RFID tag, for example, of the test strip, and adjust its behavior accordingly. The test strip itself may also or alternatively include computer readable memory or the like. The reader may also utilize different calibration coefficients, temperature corrections, and other characteristics as necessary based on the test strip being utilized.

For example, temperature of the RADFET at the time of reading may impact the accuracy of the measurement. Accordingly, in some embodiments, it may be desirable to determine temperature of the RADFET, reader, and/or the environment. In one embodiment, the test strip 400 may include a temperature sensor. In another embodiment, a temperature sensor may be built into the reader, and/or a temperature sensing element may be incorporated into the RADFET itself. With temperature determined, the reader may, in some embodiments, apply a known scaling factor based on the temperature measured. In other embodiments, the temperature determined may be utilized to modify the injected current into the RADFET to best minimize the expected temperature effects.

In some embodiments, the RADFETs may be manufactured in such a manner that each is individually calibrated to know, among other things, a more precise individual RADFET relationship between radiation exposure and the resulting change in voltage. Individual calibrations could then be communicated to the reader (for example, via settings programmed in the test strip, a database linking test strips to individual calibrations, or other techniques) and utilized during measurement to obtain even more precise readings.

Additionally, it may be desirable to "pre-measure" the RADFETs and/or test strips to determine, before use on a patient, any existing dose level to account for any dose accumulated before use. In some embodiments, a pre-measurement may be taken and then following use, the pre-measurement subtracted away to further improve accuracy of the measurement of the dose accumulated during the time period of interest (e.g., during a procedure with a patient).

Dosimetry Calculation Methods

The dosimetry may be determined using multiple methods. In some embodiments, dosimetry may be determined using mathematical methods such as, for example, methods recommended by the special committee on Medical Internal Radiation Dos (MIRD) of the Society of Nuclear Medicine and Molecular Imaging (SNMMI). Of course, other mathematical methods may also be utilized.

In some embodiments, dosimetry may be determined by calculating radiation absorbed doses (Gy) in representative volumes ($cm^3$) of subdermal tissue containing infiltrated radiopharmaceutical. As discussed above, the volumes of affected subdermal tissue may change over time as the infiltrated radiopharmaceutical is cleared, and certain techniques may be utilized to account for this clearance over time.

According to some exemplary methods, an absorbed dose—$D(r_T \leftarrow r_S)$—from activity in a source region that irradiates a target region is $D(rT \leftarrow rS) = \tilde{A}(r_S,\tau)\Sigma i\Delta i\varphi i (r_T \leftarrow r_S)/m_T$, where $\tilde{A}(r_S,\tau)$ is the time-integrated activity in the source region, and $\tilde{A}(r_S,\tau) = \int \tau 0 A(rS,t)dt$, where $\Delta_i$ is the mean energy emitted per decay or transformation, where $\varphi_i(r_T \leftarrow r_S)$ is the absorbed fraction (fraction of energy emitted from a source region that deposits in a target region), and where $m_T$ is the mass of the target region. When calculating absorbed dose to infiltrated tissue, the source and target regions may be considered the same ($r_T = r_S$); i.e., the self-dose to infiltrated tissue. In some embodiments, the target region may be larger to account for tissue beyond the source volume present at any given time capable of being affected by the source volume.

Using the counts per second data from the radiation probe (or counts per other unit of time), for example, a count-rate curve may be determined. The count-rate curve may be used to determine an effective disappearance of infiltrated activity. Said another way, the count-rate curve may be used to model the combined effects of, among other things, radioactive decay and biological clearance. In some embodiments, radiation probes may be left in place long enough to gather a sufficiently complete data set of counts per unit time from extravasation through materially complete disappearance of the infiltrated radiopharmaceutical. As noted above, other probes may also be utilized, including RADFETs, modified RADFET devices, or other imaging techniques could be employed.

In other embodiments, a more limited data set may be captured by the radiation probe(s), for example, and curve fitting or other techniques may be used to effectively extrapolate a complete data set. Such techniques may rely on curve-fitting alone, or may take advantage of a broader data set of other known extravasations in a population or other set of similar patients, for example, to better extrapolate a count-rate curve based on the partial data set measured by the probe(s). Regardless of the method used, the count-rate curve (or accumulated dose curve, for example) determined may ultimately be utilized to determine a total number of counts emanating from the site of the extravasation from injection through complete disappearance (or accumulated dose or other similar measurement). As discussed, a total probe count (or total accumulated dose) may be determined, for example, by keeping the probe(s) in place for a time from injection to complete disappearance, or by leaving the probe(s) in place for a portion of such time period and extrapolating a complete curve and integrating to find the area under the curve (i.e., total counts, total dose, etc.).

Because the probe(s) only capture a fraction of the energy released from the extravasation, it may be necessary to convert the measured counts into an estimation of absolute activity so as to understand the complete exposure to the tissue of interest. In accordance with these exemplary methods, absolute activity (measured for example in becquerel (Bq) units or MBq) may be determined from the radiation probe counts and/or count-rate curve (or accumulated dose curve, for example) using a known or estimated three-dimensional region of interest (ROI); for example, the three-dimensional area of the extravasation.

The ROI may be determined in a number of different ways. For example, the ROI may be determined directly from a patient's nuclear medicine image so long as the injection site (i.e., the site of the extravasation) is included within the image. Where the ROI may be determined directly from the patient's image, an activity calibration factor may be determined by, for example, dividing the measured count-rate at the time the image was taken by the ROI activity measured in the image at the same time. The measured or fitted count-rate curve may then by multiplied by this calibration factor to yield an absolute activity curve as a function of time and/or otherwise determine an absolute activity from the ROI.

For many reasons, however, the injection site may not be included within the image (i.e., it is outside the image's field of view) and the activity from the ROI may therefore need to be determined in another manner. In some embodiments, the activity from the ROI may be determined using one or more of the techniques. For example, extravasated activity may be estimated based on overall image quality relative to a non-extravasated infusion in one or more similar patients.

In some embodiments, volume estimation techniques using radiation probes as already discussed herein may be employed. Such techniques may lessen (or eliminate) the need to estimate the rate of clearance and/or reference an independent measurement of activity in a region of interest (e.g., from a SPECT or PET image). For example, as discussed in U.S. Patent Pub. No. 2021/0015434, a plurality of probes arranged in a known geometry may be utilized, along with various techniques, to quantify the magnitude, location, and volume of radioactive material in the body. In such embodiments, by measuring the magnitude and volume of the region of interest as a function of time, and the volume of activity in each measured voxel, the dose delivered to the tissue in each voxel volume may be determined for each sampling period. The total dose may then be obtained by adding the dose for each sampling period in each voxel. Extrapolation techniques may be employed to account for dose delivered after removal of the probes, etc.

Referring again to the MIRD schema outlined in general above, the absorbed energy fraction—$(\varphi_i(r_T \leftarrow r_S)$—may be determined in one of several different ways. In some embodiments, the absorbed energy fraction may be determined experimentally using calibration sources and phantoms. In other embodiments, the absorbed fraction may be determined using Monte Carlo track simulations or the like. However, utilizing experimental data and knowledge of the tissue in which the extravasation is located (determined, for example, via imaging or other techniques discussed herein), an absorbed energy fraction may be determined. For example, because the absorbed energy fraction is substantially similar in various tissues, and the tissues within the ROI may be determined using imaging or other techniques, the absorbed energy fraction may be determined. In some embodiments, CT scans may be used to determine density of the tissue of interest, which can help determine absorbed energy fraction based on radiation type and/or energy.

Having determined the forgoing, dosimetry to tissue within and surrounding the extravasation may be determined, in some embodiments, the absorbed dose may be measured in Gray (Gy) or other suitable unit representing the absorption of radiation energy within the tissue (e.g., absorption of energy per unit mass of tissue). In embodiments seeking to determine the risk of injury from radiation exposure from extravasations, it is typically desirable to understand how much energy was absorbed by the affected tissue. The mass of the relevant tissue may be determined by the volume of the extravasated radiopharmaceuticals in addition to the additional area into which the radiation may penetrate into, for example, subdermal fascia or other tissue, etc., of interest. An absorbed dose may then be determined by accounting for, among other things, the mass of such tissue, the total energy emitted in the source region, and fraction of the energy absorbed.

Additionally, because extravasations typically occur near the skin, it may also be desirable to determine a skin dose for, among other things, determining whether certain skin dose thresholds have been exceeded. For example, the National Council on Radiation Protection and Measurements recommends for occupational exposure that the absorbed dose in skin at a depth of 70 m be limited to 0.5 Gy averaged over the most highly exposed 10 cm$^2$ of skin. Additionally, skin dose assessments in units of shallow dose equivalent (Sv) are required by the Code of Federal Regulations in 10 CFR 20.1201(c) for a contiguous 10 cm$^2$ area of skin at a tissue depth of 0.007 cm (7 mg cm$^{-2}$). For many types of radiation involved with radiopharmaceuticals, dose expressed in units of Gray (Gy) and the shallow dose equivalent Sievert (Sv) are approximately equivalent.

Using the systems and methods taught herein, physicians and clinicians may not only promptly determine that an extravasation has occurred, but also quantifiably determine the radiation exposure risk to the patient, and whether, for example, established radiation exposure thresholds have been exceeded. This advantageously enables better and more prompt patient treatment, and also enables facilities to comply with radiation exposure reporting guidelines set by relevant authorities. All this, without the need for continuous and impractical monitoring from expensive nuclear imaging apparatus, but with low cost devices that can easily be utilizing before, during, and after nuclear imaging sessions.

The invention may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

What is claimed is:

1. A method of determining patient-specific extravasation dosimetry, comprising:
   a. determining a count-rate curve over a time-period of interest using one or more radiation probes positioned proximate a region of interest;
   b. determining a calibration factor for converting the count-rate curve to an absolute activity curve, wherein the calibration factor is determined by dividing the count rate at an imaging time by total activity from the region of interest;
   c. determine an absorbed energy fraction based on tissue characteristics and the size and location of the region of interest;
   d. determine absorbed dose to infiltrated tissue by summing total energy emitted in region of interest based on the count rate curve and calibration factor and absorbed energy fraction.

2. A method of determining patient-specific extravasation dosimetry, comprising:
   a. determining an accumulated dose curve over a time-period of interest using one or more radiation test strips positioned proximate a region of interest;
   b. determining a calibration factor for converting the accumulated dose curve to an absolute dose curve, wherein the calibration factor is determined by dividing the instantaneous dose at an imaging time by total activity from the region of interest;
   c. determine an absorbed energy fraction based on tissue characteristics and the size and location of the region of interest;
   d. determine absorbed dose to infiltrated tissue by summing total energy emitted in region of interest based on the accumulated dose curve and calibration factor and absorbed energy fraction.

3. The method of claim 2, wherein the one or more test strips comprise a plurality of RADFETs, and further wherein terminals of the RADFETs are electrically coupled together.

4. The method of claim 3, further comprising the step of removing the one or more test strips from the patient after the time-period of interest and inserting the test strips into a reader, wherein the reader is configured to sever the electrical connection between the terminals of the plurality of RADFETs, inject a current into each of the plurality of RADFETs, and measure a voltage at each of the plurality of RADFETs.

5. The method of claim 2, wherein the test strip is coupled to a reader configured to sever the electrical connection between the terminals of the plurality of RADFETs, inject a current into each of the plurality of RADFETs, and measure a voltage at each of the plurality of RADFETs.

6. The method of claim 5 further comprising the step of re-connecting the electrical connection between the terminals of the plurality of RADFETs.

7. The method of claim 2, further comprising the step of displaying or communicating the absorbed dose.

* * * * *